United States Patent [19]
Kim et al.

[11] Patent Number: 5,720,976
[45] Date of Patent: Feb. 24, 1998

[54] THERMOSENSITIVE LIPOSOME AND PROCESS FOR PREPARING THE SAME

[75] Inventors: Jong-Duk Kim; Jin-Chul Kim, both of Taejon; Soo-Kyoung Bae, Seoul, all of Rep. of Korea

[73] Assignee: Korea Advanced Institute of Science and Technology, Yusong-ku, Rep. of Korea

[21] Appl. No.: 783,113

[22] Filed: Jan. 14, 1997

[30] Foreign Application Priority Data

Jan. 30, 1996 [KR] Rep. of Korea .................. 96-2103

[51] Int. Cl.$^6$ ................................................ A61K 9/127
[52] U.S. Cl. ..................... 424/450; 264/4.1; 264/4.3; 264/4.33
[58] Field of Search .................... 424/450; 264/4.1, 264/4.3, 4.33

[56] References Cited

U.S. PATENT DOCUMENTS

| | | | |
|---|---|---|---|
| 4,804,539 | 2/1989 | Guo | 424/450 |
| 5,008,109 | 4/1991 | Tin | 424/422 |

OTHER PUBLICATIONS

T. Tomita et al., "Temperature–Sensitive Release of Adriamycin, an Amphiphilic Antitumor Agent, from Dipalmitoylphosphatidylcholine–Cholesterol Liposomes", *Biochim. Biophys. Acta*, 978:185–190(1989).

N. Oku et al., "Potential Usage of Thermosensitive Liposomes for Macromolecule Delivery", *Biochim. Biophys. Acta*, 1191: 389391(1994).

K. Kono et al., "Temperature–Sensitive Liposomes: Liposomes Bearing poly (N–isopropylacrylamide)", *Journal of Controlled Release*, 30:69–75(1994).

K. Maruyama et al., "Enhanced Delivery of Doxorubicin to Tumor by Long–Circulating Thermosensitive Liposomes and Local Hyperthermia", *Biochim. Biophys. Acta*, 1149:209–216(1993).

J. N. Weinstein et al., "Phase Transition Release, a New Approach to The Interaction of Proteins with Lipid Vesicles", *Biochim. Biophys. Acta*, 647:270–284(1981).

*Primary Examiner*—Gollamudi S. Kishore
*Attorney, Agent, or Firm*—Darby & Darby

[57] ABSTRACT

The present invention provides a thermosensitive liposome which permits temperature-sensitive drug release and exhibits variable release temperatures. The process for preparing a thermosensitive liposome of the invention, comprises a step of coating the surface of a liposome with a copolymer of N-isopropylacrylamide/octadecylacrylate/acrylic acid, by the addition of the copolymer to the liposome suspension in a weight ratio of 1:0.05 to 1:0.2 (liposome:copolymer), and the incubation of the polymer-liposome suspension at a temperature range of 0° to 10° C., for 10 to 14 hours. The thermosensitive liposome of the present invention is able to control the temperature of drug release at a temperature range of above 28° C., preferably at 28° to 36° C., depending on the acrylic acid content in the copolymer of N-isopropylacrylamide/octadecylacrylate/acrylic acid.

5 Claims, 2 Drawing Sheets

THERMOSENSITIVE LIPOSOME AND PROCESS FOR PREPARING THE SAME

FIELD OF THE INVENTION

The present invention relates to a thermosensitive liposome which exhibits variable release temperatures, more specifically, to a thermosensitive liposome coated with copolymer of N-isopropylacrylamide/octadecylacrylate/acrylic acid which exhibits variable release temperatures, and a process for preparing the same.

BACKGROUND OF THE INVENTION

A variety of thermosensitive liposomes have been known in the art. For example, a liposome consisting of anionic detergent and phospholipid which releases drugs rapidly at a temperature range of 40° to 45° C., and a liposome consisting of dipalmitoylphosphatidylcholine(DPPC) and 1,2-diacylglycerophospholipid which releases drugs effectively at a temperature range of 40° to 44° C., have been reported(see: Japanese unexamined patent publication (Hei) 06-227966).

In addition, K. Kono et al. teaches a thermosensitive liposome which starts to release drugs at a temperature range of 25° to 30° C., i.e., lecithin or DPPC-containing liposome coated with copolymer of N-isopropylacrylamide/octadecylacrylate(see: K. Kono et al., J. Controlled Release, 30:69–75(1994)).

The liposome coated with copolymer of N-isopropylacrylamide/octadecylacrylate, however, is proven less satisfactory in the senses that: the release temperature of the liposome can not be controlled; and, stability of the liposome is not fully guaranteed at room temperature, since drug release is allowed even at a relatively low temperature near room temperature.

SUMMARY OF THE INVENTION

In accordance with the present invention, the inventors have made an effort to prepare a thermosensitive liposome which permits temperature-sensitive drug release, and discovered that drug-entrapped liposomes coated with copolymer of N-isopropylacrylamide/octadecylacrylate/acrylic acid, start to release drugs at variable temperatures by controlling the acrylic acid content in the copolymer.

A primary object of the present invention is, therefore, to provide a process for preparing a thermosensitive liposome which exhibits variable release temperatures at a temperature range of above room temperature.

The other object of the invention is to provide the thermosensitive liposome which exhibits variable release temperatures.

BRIEF DESCRIPTION OF DRAWINGS

The above and the other objects and features of the present invention will become apparent from the following description given in conjunction with the accompanying drawings, in which.

DETAILED DESCRIPTION OF THE INVENTION

Figure 1:
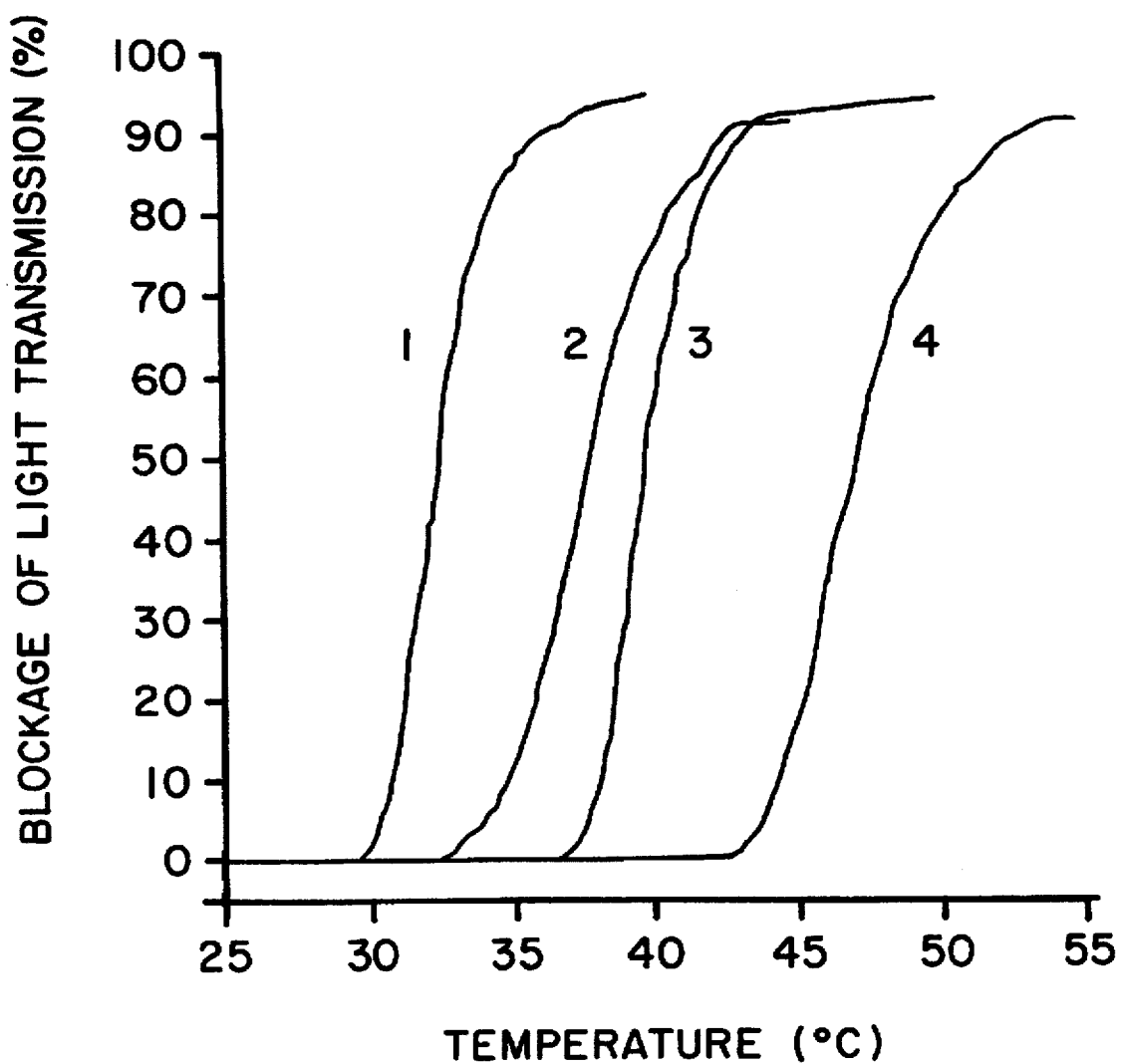
FIG. 1 is a graph showing lower critical solution temperature of copolymers of N-isopropylacrylamide/octadecylacrylate/acrylic acid represented as the level of blockage of light transmission in accordance with the temperature change.

To accomplish the primary object of the present invention, a process for preparing a thermosensitive liposome which exhibits variable release temperatures, comprises a step of coating the surface of a liposome with a copolymer of N-isopropylacrylamide/octadecylacrylate/acrylic acid by adding the said copolymer to drug-entrapped liposome suspension.

In accordance with the process for preparing a thermosensitive liposome of the invention, any drug used in liposome preparation can be employed, and any liposome conventionally known in the art can be employed, though lecithin or DPPC-containing liposomes are preferred.

The molar ratio of N-isopropylacrylamide/octadecylacrylate/acrylic acid may be 9.9/0.1/0.1 to 9.9/0.1/0.4, preferably 9.9/0.1/0.11 to 9.9/0.1/0.33. The copolymer of N-isopropylacrylamide/octadecylacrylate/acrylic acid is prepared by dissolving the mixture of N-isopropylacrylamide/octadecylacrylate/acrylic acid and AIBN($\alpha,\alpha'$azobisisobutyronitrile) in an organic solvent such as dioxane, removing the gas dissolved in the organic solvent by inflow of nitrogen, stirring the reaction solution for 12 hours at a constant temperature of 70° C. to induce copolymerization, adding diethylether to the solution and filtering to obtain the synthesized copolymer.

In the process for preparing a thermosensitive liposome of the invention, the step of coating the surface of the liposome with the said copolymer, comprises the addition of the copolymer to the suspension of liposome, and the incubation of the copolymer-liposome suspension.

Entrapment of drug into liposome and preparation of drug-entrapped liposome suspension are carried out, according to the conventional method in the art. For example, if calcein and lecithin are employed as a model drug and a liposomal material, respectively, calcein is dissolved in a phosphate buffer(pH 7.4) in a concentration of 10 to 100 mM, preferably 30 to 70 mM, more preferably 40 to 60 mM, to prepare a drug-containing solution. Then, the drug-containing solution and the dry film of lecithin are mixed in a ratio of 1:200 (w/v), and the lecithin film is dispersed and sonicated for 5 to 30 minutes at room temperature, finally to prepare desired drug-entrapped liposome suspension.

To the drug-entrapped liposome suspension thus prepared is added copolymer of N-isopropylacrylamide/octadecylacrylate/acrylic acid, in a weight ratio of 1:0.05 to 1:0.2 (liposome:copolymer), preferably 1:0.1, where the copolymer is prepared by copolymerizing monomers of N-isopropylacrylamide/octadecylacrylate/acrylic acid mixed in a molar ratio of 9.9/0.1/0.1 to 9.9/0.1/0.4, preferably 9.9/0.1/0.11 to 9.9/0.1/0.33. Then, the mixture is incubated at 0° to 10° C., preferably 2° to 5° C., for 10 to 14 hours, to give liposome whose surface is coated with the copolymer.

The thermosensitive liposome coated with copolymer of N-isopropylacrylamide/octadecylacrylate/acrylic acid of the invention, exhibits variable release temperatures above 28° C., preferably ranging from 28° to 36° C., by controlling acrylic acid content in the copolymer, e.g., by controlling a molar ratio of acrylic acid in a range of 0.1 to 0.4, preferably 0.11 to 0.33, against that of N-isopropylacrylamide/octadecylacrylate of 9.9/0.1.

The thermosensitive liposome of the invention, compared to the conventional thermosensitive lecithin or DPPC-containing liposome coated with copolymer of N-isopropylacrylamide/octadecylacrylate, has following advantages(see: K. Kono et al., J. controlled Release, 30:69–75(1994)):

1. Ability to Control the Temperature of Drug Release

While the conventional thermosensitive liposome coated with copolymer of N-isopropylacrylamide/ octadecylacrylate starts to release drugs at a temperature of below 28° C., the thermosensitive liposome of the invention elevates the temperature of drug release to 36° C., i.e. above 28° C., by controlling the acrylic acid content in the copolymer.

2. Stability at Room Temperature

Since the conventional thermosensitive liposome coated with copolymer of N-isopropylacrylamide/ octadecylacrylate starts to release drugs at a temperature of below 28° C., the liposome releases drugs during handling at room temperature. On the contrary, the thermosensitive liposome of the invention which is coated with copolymer of N-isopropylacrylamide/octadecylacrylate/acrylic acid, does not release drugs under a temperature of 28° C. Accordingly, the liposome of the invention is fairly stable at room temperature.

The present invention is further illustrated by the following examples, which should not be taken to limit the scope of the invention.

EXAMPLE 1: Synthesis of N-isopropylacrylamide/ octadecyl-acrylate/acrylic Acid Copolymer and Measurement of Lower Critical Solution Temperature Monomers of N-isopropylacrylamide/octadecylacrylate/ acrylic acid mixed in a molar ratio of 9.9/0.1/0, 9.9/0.1/0.11, 9.9/0.1/0.22 and 9.9/0.1/0.33, respectively, and AIBN($\alpha,\alpha'$-azobisisobutyronitrile) were dissolved in dioxane, and gas was removed from the organic solvent by inflow of nitrogen. Then, the reaction solution was stirred for 12 hours at a constant temperature of 70° C., diethylether was added, and filtered to recover the synthesized copolymer. Synthesized copolymer was dissolved in a phosphate buffer(pH 7.4) in a concentration of 5 mg/ml, and placed in a cell having a diameter of 1 cm and thickness of 2 mm. Then, lower critical solution temperature of the copolymer was measured by observing the level of light transmission in the sample, while increasing the temperature of the sample by 1° C. per minute. FIG. 1 is a graph showing lower critical solution temperature of copolymers of N-isopropylacrylamide/ octadecylacrylate/acrylic acid which are formulated in a molar ratio of 9.9/0.1/0 (curve 1), 9.9/0.1/0.11 (curve 2), 9.9/0.1/0.22 (curve 3) 9.9/0.1/0.33 (curve 4), respectively, each of which is represented as level of blockage of light transmission against the change of the temperature. As can be seen in FIG. 1, as the content of acrylic acid increased, the temperature at which the level of blockage of light transmission, that is, lower critical solution temperature increased. Also, when the acrylic acid content increased to 0 mole(curve 1), 0.11 mole(curve 2), 0.22 mole(curve 3) and 0.33 mole(curve 4) against 9.9 mole of N-isopropylacrylamide, the temperature at which the level of blockage of light transmission is 50% increased to 32.3, 37.5, 39.7 and 46.9° C., respectively.

EXAMPLE 2: Preparation of Calcein-Entrapped Liposome Coated with Copolymer of N-isopropylacrylamide/octadecyl-acrylate/acrylic Acid To 20 mg of dry film of lecithin was added 2 ml of phosphate buffer(pH 7.4) containing 50 mM calcein. Then, the dry film of lecithin was dispersed at room temperature and sonicated for 10 minutes to prepare liposome. Unentrapped calceins were removed by using Bio-Gel A-0.5 m. To calcein-entrapped liposome thus prepared were added copolymers of N-isopropylacrylamide/octadecylacrylate/ acrylic acid prepared in Example 1 having molar ratios of 9.9/0.1/0, 9.9/0.1/0.11, 9.9/0.1/0.22 and 9.9/0.1/0.33, respectively, in a weight ratio of 1:0.1 (liposome:copolymer). Then, the mixtures were incubated at a temperature of 4° C. for 12 hours to give lecithin liposome coated with copolymer of N-isopropylacrylamide/ octadecylacrylate/acrylic acid.

EXAMPLE 3: Measurement of the Rate of Calcein Release from Liposome Coated with Copolymer of N-isopropyl-acrylamide/octadecylacrylate/acrylic Acid The percentage of calcein release of the liposomes prepared in Example 2 was measured at a temperature range of 20° to 46° C. using a fluorescence spectrometer equipped with a thermal controller. For fluorescence spectrometry, 2.6 ml of phosphate buffer(pH 7.4) was placed in a 3 ml-cell to adjust the environment to a temperature of 20° C. to 46° C. Then, each of the liposome sample(0.2 ml) prepared in Example 2 whose temperature was maintained at 18° C., was added to the phosphate buffer in the cell, and the fluorescence change at 520 nm was monitored for 80 seconds using a fluorescence spectrometer. In this experiment, the excitation and emission wavelength were controlled at 490 nm and 520 nm, respectively, and the percentage(%) of calcein release was determined as following equation:

$$\text{The percentage of calcein release} = (F-F')/(F^0-F') \times 100$$

wherein,

F is the fluorescence intensity at a temperature;

$F^0$ is the fluorescence intensity at 18° C.; and,

F' is total fluorescence intensity after the addition of 0.12% deoxycholate to dissolve liposomes completely.

Figure 2:
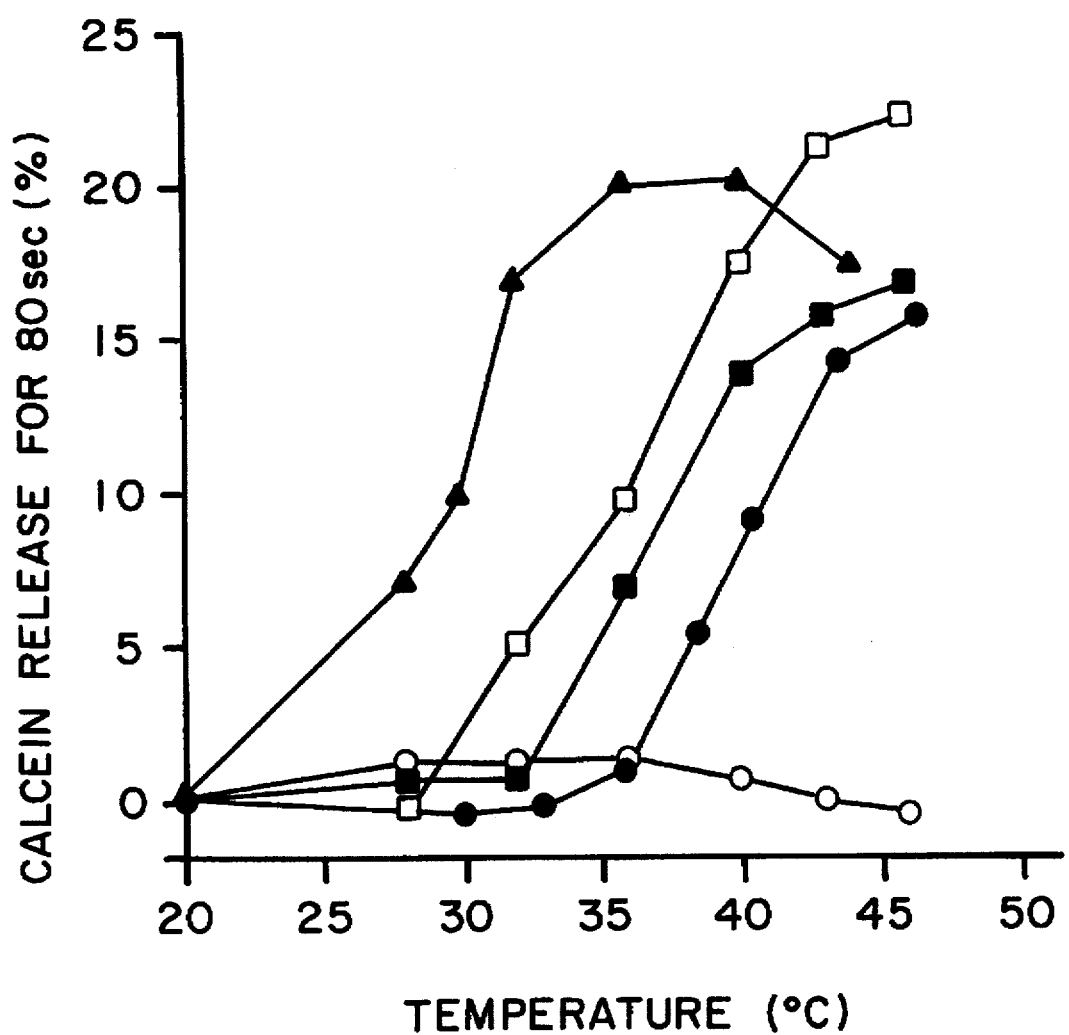
FIG. 2 is a graph showing calcein release from non-coated lecithin liposome and lecithin liposomes coated with copolymer of N-isopropylacrylamide/octadecylacrylate/acrylic acid in accordance with the temperature change.

FIG. 2 shows the percentage of calcein release in accordance with the temperature change. As shown in FIG. 2, it was found that liposomes coated with copolymers of N-isopropylacrylamide/octadecylacrylate/acrylic acid of the invention whose acrylic acid contents were 0.11 mole(▼), 0.22 mole(■) and 0.33 mole(●) and N-isopropylacrylamide contents were 9.9 mole, started to release calcein at 28° C., 32° C. and 36° C., respectively, while liposome(▲) coated with copolymer of N-isopropylacrylamide/ octadecylacrylate which is free of acrylic acid released 7% calcein at 28° C. Accordingly, it was clearly determined that the thermosensitive liposomes of the invention show variable release temperatures by controlling the acrylic acid content in the copolymer of N-isopropylacrylamide/ octadecylacrylate/acrylic acid. As shown in FIG. 2, calcein release of non-coated lecithin liposomes(○) was almost 0% over the whole range of the test temperature.

As clearly illustrated and demonstrated above, the present invention provides a thermosensitive liposome coated with copolymer of N-isopropylacrylamide/octadecylacrylate/ acrylic acid which permits temperature-sensitive drug release. The thermosensitive liposome of the invention is able to control the temperature of drug release at a temperature range of above 28° C., preferably at 28° to 36° C., depending on the acrylic acid content in the copolymer of N-isopropylacrylamide/octadecylacrylate/acrylic acid, which guarantees a good stability at room temperature, when compared to the conventional thermosensitive liposomes.

What is claimed is:

1. A process for preparing a thermosensitive liposome which exhibits variable release temperatures, which comprises the steps of:

coating the surface of a drug-entrapped liposome with a copolymer of N-isopropylacrylamide/octadecylacrylate/acrylic acid by adding the copolymer to the drug-entrapped liposome suspension in a weight ratio of 1:0.05 to 1:0.2 (liposome:copolymer); and, incubating the copolymer-liposome suspension at 0° to 10° C. for 10 to 14 hours.

2. The process for preparing a thermosensitive liposome which exhibits variable release temperatures of claim 1, wherein the copolymer of N-isopropylacrylamide/octadecylacrylate/acrylic acid has molar ratio of 9.9/0.1/0.1 to 9.9/0.1/0.4.

3. The process for preparing a thermosensitive liposome which exhibits variable release temperatures of claim 1, wherein the copolymer of N-isopropylacrylamide/octadecylacrylate/acrylic acid is prepared by: dissolving the mixture of N-isopropylacrylamide/octadecylacrylate/acrylic acid and AIBN($\alpha,\alpha'$-azobisisobutyronitrile) in an organic solvent, removing the gas dissolved in the organic solvent by inflow of nitrogen, stirring the reaction solution for 12 hours at a constant temperature of 70° C. to induce copolymerization, adding diethylether and filtering to obtain the synthesized copolymer.

4. The process for preparing a thermosensitive liposome which exhibits variable release temperatures of claim 3, wherein the organic solvent is dioxane.

5. A thermosensitive liposome which exhibits variable release temperatures, which is prepared by adding a copolymer of N-isopropylacrylamide/octadecylacrylate/acrylic acid to a drug-entrapped liposome suspension in a weight ratio of 1:0.05 to 1:0.2 (liposome:copolymer) and incubating the copolymer-liposome suspension at 0° to 10° C. for 10 to 14 hours.

* * * * *